(12) United States Patent
Caparso et al.

(10) Patent No.: US 11,351,380 B2
(45) Date of Patent: Jun. 7, 2022

(54) IMPLANTABLE STIMULATION POWER RECEIVER, SYSTEMS AND METHODS

(71) Applicant: XII Medical, Inc., Cleveland, OH (US)

(72) Inventors: Anthony V. Caparso, North Ridgeville, OH (US); Josh Nickols, Louisville, KY (US); Steven M. Young, Ann Arbor, MI (US)

(73) Assignee: XII MEDICAL, INC., Cleveland, OH (US)

( * ) Notice: Subject to any disclaimer, the term of this patent is extended or adjusted under 35 U.S.C. 154(b) by 0 days.

(21) Appl. No.: 16/865,541

(22) Filed: May 4, 2020

(65) Prior Publication Data
US 2020/0346024 A1 Nov. 5, 2020

Related U.S. Application Data

(60) Provisional application No. 62/841,978, filed on May 2, 2019.

(51) Int. Cl.
*A61N 1/00* (2006.01)
*A61N 1/36* (2006.01)
(Continued)

(52) U.S. Cl.
CPC ....... *A61N 1/36139* (2013.01); *A61N 1/0548* (2013.01); *A61N 1/3611* (2013.01);
(Continued)

(58) Field of Classification Search
USPC .......................................... 607/61
See application file for complete search history.

(56) References Cited

U.S. PATENT DOCUMENTS 4,990,160 A 2/1991 Terino
5,591,216 A 1/1997 Testerman et al.
(Continued)

FOREIGN PATENT DOCUMENTS

JP 2013-208182 A 10/2013
WO WO-92/19318 A1 11/1992
(Continued)

OTHER PUBLICATIONS

Björninen, T., Merilampi, S., Ukkonen, L., Sydänheimo, L., & Ruuskanen, P. (2009). The effect of fabrication method on passive UHF RFID tag performance. International Journal of Antennas and Propagation, 2009, 1-8. https://doi.org/10.1155/2009/920947 (Year: 2009).*

(Continued)

*Primary Examiner* — John R Downey
*Assistant Examiner* — Anant A Gupta
(74) *Attorney, Agent, or Firm* — Fortem IP LLP; Mary L. Fox; Katrina Marcelo (57) ABSTRACT

A wireless implantable neuromuscular stimulator includes an antenna for producing an induced current in response to being disposed in an electromagnetic field. The antenna includes a substrate having an upper surface and a lower surface. An upper coil including a plurality of coil turns is disposed on the upper surface of the substrate. A lower coil including a plurality of coil turns is disposed on the lower surface of the substrate. The upper and lower coils are electrically connected to each other in parallel. The parallel connection can be facilitated by a plurality of connectors that extend through the substrate and electrically connect the upper coil to the lower coil. In one example configuration, connectors connect each coil turn of the upper coil to a corresponding turn of the lower coil.

20 Claims, 8 Drawing Sheets

(51) Int. Cl.
*A61N 1/05* (2006.01)
*A61N 1/372* (2006.01)
*A61B 5/11* (2006.01)
*A61B 5/00* (2006.01)
*A61B 5/394* (2021.01)

(52) U.S. Cl.
CPC ......... *A61N 1/37229* (2013.01); *A61B 5/1114* (2013.01); *A61B 5/1116* (2013.01); *A61B 5/394* (2021.01); *A61B 5/4552* (2013.01); *A61B 5/4812* (2013.01); *A61B 5/4818* (2013.01); *A61N 1/37211* (2013.01)

(56) References Cited

U.S. PATENT DOCUMENTS

| | | |
|---|---|---|
| 5,609,621 A | 3/1997 | Bonner |
| 5,716,377 A | 2/1998 | Rise et al. |
| 5,877,466 A | 3/1999 | Bolongeat-Mobleu et al. |
| 5,988,171 A | 11/1999 | Sohn et al. |
| 6,240,316 B1 | 5/2001 | Richmond et al. |
| 6,587,725 B1 | 7/2003 | Durand et al. |
| 6,770,022 B2 | 8/2004 | Mechlenburg et al. |
| 7,660,632 B2 | 2/2010 | Kirby et al. |
| 7,668,591 B2 | 2/2010 | Lee et al. |
| 7,711,438 B2 | 5/2010 | Lettner et al. |
| 7,885,713 B2 | 2/2011 | Campbell |
| 8,255,056 B2 | 8/2012 | Tehrani |
| 8,498,712 B2 | 7/2013 | Bolea et al. |
| 8,498,713 B2 | 7/2013 | McClure et al. |
| 8,574,164 B2 | 11/2013 | Mashiach |
| 8,577,464 B2 | 11/2013 | Mashiach |
| 8,577,465 B2 | 11/2013 | Mashiach |
| 8,577,466 B2 | 11/2013 | Mashiach |
| 8,577,467 B2 | 11/2013 | Mashiach et al. |
| 8,577,468 B2 | 11/2013 | Mashiach et al. |
| 8,577,472 B2 | 11/2013 | Mashiach et al. |
| 8,577,478 B2 | 11/2013 | Mashiach et al. |
| 8,577,647 B2 | 11/2013 | Farritor et al. |
| 8,585,617 B2 | 11/2013 | Mashiach et al. |
| 8,588,941 B2 | 11/2013 | Mashiach |
| 8,626,304 B2 | 1/2014 | Bolea et al. |
| 8,644,957 B2 | 2/2014 | Mashiach |
| 8,700,183 B2 | 4/2014 | Mashiach |
| 8,718,776 B2 | 5/2014 | Mashiach et al. |
| 8,744,589 B2 | 6/2014 | Bolea et al. |
| 8,751,005 B2 | 6/2014 | Meadows et al. |
| 8,798,773 B2 | 8/2014 | Mashiach |
| 8,812,113 B2 | 8/2014 | Mashiach |
| 8,812,135 B2 | 8/2014 | Mashiach |
| 8,831,730 B2 | 9/2014 | Mashiach et al. |
| 8,838,256 B2 | 9/2014 | Mashiach et al. |
| 8,897,880 B2 | 11/2014 | Mashiach |
| 8,897,895 B2 | 11/2014 | Mashiach |
| 8,903,493 B2 | 12/2014 | Mashiach et al. |
| 8,903,515 B2 | 12/2014 | Mashiach |
| 8,948,871 B2 | 2/2015 | Mashiach et al. |
| 8,958,893 B2 | 2/2015 | Mashiach |
| 8,989,868 B2 | 3/2015 | Mashiach et al. |
| 9,031,653 B2 | 5/2015 | Mashiach |
| 9,031,654 B2 | 5/2015 | Meadows et al. |
| 9,044,612 B2 | 6/2015 | Mashiach et al. |
| 9,061,151 B2 | 6/2015 | Mashiach et al. |
| 9,061,162 B2 | 6/2015 | Mashiach et al. |
| 9,095,725 B2 | 8/2015 | Mashiach |
| 9,101,774 B2 | 8/2015 | Mashiach et al. |
| 9,155,899 B2 | 10/2015 | Mashiach et al. |
| 9,186,511 B2 | 11/2015 | Bolea |
| 9,220,907 B2 | 12/2015 | Mashiach et al. |
| 9,220,908 B2 | 12/2015 | Mashiach |
| 9,248,290 B2 | 2/2016 | Mashiach |
| 9,248,291 B2 | 2/2016 | Mashiach |
| 9,248,302 B2 | 2/2016 | Mashiach et al. |
| 9,259,585 B2 | 2/2016 | Vajha et al. |
| 9,302,093 B2 | 4/2016 | Mashiach |
| 9,308,370 B2 | 4/2016 | Lima et al. |
| 9,308,381 B2 | 4/2016 | Mashiach et al. |
| 9,314,613 B2 | 4/2016 | Mashiach |
| 9,314,641 B2 | 4/2016 | Meadows et al. |
| 9,327,132 B2 | 5/2016 | Mashiach |
| 9,339,651 B2 | 5/2016 | Meadows et al. |
| 9,358,392 B2 | 6/2016 | Mashiach |
| 9,370,657 B2 | 6/2016 | Tehrani et al. |
| 9,393,435 B2 | 7/2016 | Mashiach |
| 9,403,009 B2 | 8/2016 | Mashiach |
| 9,403,025 B2 | 8/2016 | Mashiach et al. |
| 9,409,013 B2 | 8/2016 | Mashiach et al. |
| 9,415,215 B2 | 8/2016 | Mashiach |
| 9,415,216 B2 | 8/2016 | Mashiach |
| 9,421,372 B2 | 8/2016 | Mashiach et al. |
| 9,463,318 B2 | 10/2016 | Mashiach et al. |
| 9,486,628 B2 | 11/2016 | Christopherson et al. |
| 9,757,560 B2 | 9/2017 | Papay |
| 9,849,288 B2 | 12/2017 | Meadows et al. |
| 9,950,166 B2 | 4/2018 | Mashiach et al. |
| 10,029,098 B2 | 7/2018 | Papay |
| 10,065,038 B2 | 9/2018 | Papay |
| 10,105,538 B2 | 10/2018 | Bolea et al. |
| 10,238,468 B2 | 3/2019 | Forsell |
| 10,675,467 B2 | 6/2020 | Papay |
| 2002/0010495 A1 | 1/2002 | Freed et al. |
| 2006/0224211 A1 | 10/2006 | Durand et al. |
| 2007/0160274 A1 | 7/2007 | Mashiach |
| 2007/0263915 A1 | 11/2007 | Mashiach |
| 2008/0260229 A1 | 10/2008 | Mashiach |
| 2009/0082831 A1 | 3/2009 | Paul et al. |
| 2009/0226057 A1 | 9/2009 | Mashiach et al. |
| 2009/0270960 A1 | 10/2009 | Zhao et al. |
| 2010/0094379 A1 | 4/2010 | Meadows et al. |
| 2010/0179562 A1 | 7/2010 | Linker et al. |
| 2010/0241195 A1 | 9/2010 | Meadows et al. |
| 2010/0260217 A1 | 10/2010 | Redford |
| 2010/0280568 A1 | 11/2010 | Bulkes et al. |
| 2010/0292769 A1 | 11/2010 | Brounstein et al. |
| 2011/0071606 A1 | 3/2011 | Kast et al. |
| 2011/0093036 A1 | 4/2011 | Mashiach |
| 2011/0230702 A1 | 9/2011 | Honour |
| 2012/0010532 A1 | 1/2012 | Bolea et al. |
| 2013/0085537 A1 | 4/2013 | Mashiach |
| 2013/0085558 A1 | 4/2013 | Mashiach |
| 2013/0204097 A1 | 8/2013 | Rondoni et al. |
| 2013/0289401 A1 | 10/2013 | Colbaugh et al. |
| 2014/0031840 A1 | 1/2014 | Mashiach |
| 2014/0031902 A1 | 1/2014 | Mashiach |
| 2014/0031903 A1 | 1/2014 | Mashiach |
| 2014/0031904 A1 | 1/2014 | Mashiach |
| 2014/0046221 A1 | 2/2014 | Mashiach et al. |
| 2014/0052219 A1 | 2/2014 | Mashiach et al. |
| 2014/0100642 A1 | 4/2014 | Mashiach |
| 2014/0135868 A1 | 5/2014 | Bashyam |
| 2014/0172061 A1 | 6/2014 | Mashiach |
| 2014/0266933 A1* | 9/2014 | Andersen .............. H01Q 1/273 343/718 |
| 2014/0358026 A1 | 12/2014 | Mashiach et al. |
| 2014/0358189 A1 | 12/2014 | Mashiach et al. |
| 2014/0358196 A1 | 12/2014 | Mashiach |
| 2014/0358197 A1 | 12/2014 | Mashiach et al. |
| 2014/0371802 A1 | 12/2014 | Mashiach et al. |
| 2014/0371817 A1 | 12/2014 | Mashiach et al. |
| 2014/0379049 A1 | 12/2014 | Mashiach et al. |
| 2015/0032177 A1 | 1/2015 | Mashiach et al. |
| 2015/0073232 A1 | 3/2015 | Ahmad et al. |
| 2015/0077308 A1* | 3/2015 | Jeon .................... H01Q 1/36 343/895 |
| 2015/0088025 A1* | 3/2015 | Litvak .................. A61B 5/316 600/546 |
| 2015/0096167 A1 | 4/2015 | Zhao et al. |
| 2015/0112402 A1 | 4/2015 | Mashiach |
| 2015/0112416 A1* | 4/2015 | Mashiach ........... H04B 5/0037 607/134 |
| 2015/0142120 A1 | 5/2015 | Papay |
| 2015/0224307 A1 | 8/2015 | Bolea |
| 2015/0265221 A1 | 9/2015 | Flanagan et al. |
| 2015/0283313 A1 | 10/2015 | Huber |

(56) References Cited

U.S. PATENT DOCUMENTS

| | | | |
|---|---|---|---|
| 2015/0290465 A1 | 10/2015 | Mashiach | |
| 2015/0343221 A1 | 12/2015 | Mashiach | |
| 2016/0094082 A1* | 3/2016 | Ookawa | H01F 38/14 |
| | | | 320/108 |
| 2016/0106976 A1 | 4/2016 | Kucklick | |
| 2016/0121121 A1 | 5/2016 | Mashiach | |
| 2016/0121122 A1 | 5/2016 | Mashiach | |
| 2016/0175587 A1 | 6/2016 | Lima et al. | |
| 2016/0184583 A1 | 6/2016 | Meadows et al. | |
| 2016/0235990 A1 | 8/2016 | Mashiach | |
| 2016/0346537 A1 | 12/2016 | Mashiach | |
| 2017/0087360 A1 | 3/2017 | Scheiner | |
| 2017/0143280 A1 | 5/2017 | Kent et al. | |
| 2017/0290699 A1 | 10/2017 | Radmand | |
| 2018/0015282 A1 | 1/2018 | Waner et al. | |
| 2018/0028824 A1 | 2/2018 | Pivonka et al. | |
| 2018/0117313 A1 | 5/2018 | Schmidt et al. | |
| 2018/0191069 A1* | 7/2018 | Chen | H01Q 1/38 |
| 2018/0200512 A1 | 7/2018 | Bolea et al. | |
| 2018/0221673 A1* | 8/2018 | Kuang | A61N 1/36038 |
| 2019/0151656 A1 | 5/2019 | Bolea et al. | |
| 2019/0160282 A1 | 5/2019 | Dieken et al. | |
| 2019/0247664 A1* | 8/2019 | Irazoqui | A61B 5/08 |
| 2020/0016401 A1 | 1/2020 | Papay et al. | |
| 2020/0269044 A1 | 8/2020 | Papay | |
| 2020/0346010 A1 | 11/2020 | Papay et al. | |
| 2020/0346016 A1 | 11/2020 | Parse et al. | |
| 2020/0346017 A1 | 11/2020 | Caparso et al. | |
| 2021/0106824 A1 | 4/2021 | Caparso et al. | |
| 2021/0128914 A1 | 5/2021 | Papay | |

FOREIGN PATENT DOCUMENTS

| | | |
|---|---|---|
| WO | WO-2005/018737 A1 | 3/2005 |
| WO | WO-2007/080579 A2 | 7/2007 |
| WO | WO-2007/080579 A3 | 7/2007 |
| WO | WO-2007/080580 A2 | 7/2007 |
| WO | WO-2007/080580 A3 | 7/2007 |
| WO | WO-2008/129545 A1 | 10/2008 |
| WO | WO-2009/007896 A2 | 1/2009 |
| WO | WO-2009/007896 A3 | 1/2009 |
| WO | WO-2009/109971 A2 | 9/2009 |
| WO | WO-2009/109971 A3 | 9/2009 |
| WO | 2009/143560 A1 | 12/2009 |
| WO | 2010/006218 A2 | 1/2010 |
| WO | WO-2011/048590 A1 | 4/2011 |
| WO | WO-2011/077433 A1 | 6/2011 |
| WO | WO-2013/046032 A2 | 4/2013 |
| WO | WO-2013/046032 A3 | 4/2013 |
| WO | WO-2013/046035 A2 | 4/2013 |
| WO | WO-2013/046035 A3 | 4/2013 |
| WO | WO-2013/046038 A2 | 4/2013 |
| WO | WO-2013/046038 A3 | 4/2013 |
| WO | WO-2013/046039 A2 | 4/2013 |
| WO | WO-2013/046039 A3 | 4/2013 |
| WO | WO-2013/046040 A2 | 4/2013 |
| WO | WO-2013/046040 A3 | 4/2013 |
| WO | WO-2013/046042 A2 | 4/2013 |
| WO | WO-2013/046042 A3 | 4/2013 |
| WO | WO-2013/046043 A2 | 4/2013 |
| WO | WO-2013/046043 A3 | 4/2013 |
| WO | WO-2013/046044 A2 | 4/2013 |
| WO | WO-2013/046044 A3 | 4/2013 |
| WO | WO-2013/046048 A2 | 4/2013 |
| WO | WO-2013/046048 A3 | 4/2013 |
| WO | WO-2013/046049 A2 | 4/2013 |
| WO | WO-2013/046049 A3 | 4/2013 |
| WO | WO-2013/046053 A2 | 4/2013 |
| WO | WO-2013/046053 A3 | 4/2013 |
| WO | WO-2013/057594 A2 | 4/2013 |
| WO | WO-2013/057594 A3 | 4/2013 |
| WO | WO-2013/061164 A2 | 5/2013 |
| WO | WO-2013/061164 A3 | 5/2013 |
| WO | WO-2013/061169 A2 | 5/2013 |
| WO | WO-2013/061169 A3 | 5/2013 |
| WO | WO-2013/177621 A1 | 12/2013 |
| WO | WO-2014/016684 A2 | 1/2014 |
| WO | WO-2014/016684 A3 | 1/2014 |
| WO | WO-2014/016686 A2 | 1/2014 |
| WO | WO-2014/016686 A3 | 1/2014 |
| WO | WO-2014/016687 A2 | 1/2014 |
| WO | WO-2014/016687 A3 | 1/2014 |
| WO | WO-2014/016688 A2 | 1/2014 |
| WO | WO-2014/016688 A3 | 1/2014 |
| WO | WO-2014/016691 A2 | 1/2014 |
| WO | WO-2014/016691 A3 | 1/2014 |
| WO | WO-2014/016692 A2 | 1/2014 |
| WO | WO-2014/016692 A3 | 1/2014 |
| WO | WO-2014/016693 A2 | 1/2014 |
| WO | WO-2014/016693 A3 | 1/2014 |
| WO | WO-2014/016694 A2 | 1/2014 |
| WO | WO-2014/016694 A3 | 1/2014 |
| WO | WO-2014/016697 A2 | 1/2014 |
| WO | WO-2014/016697 A3 | 1/2014 |
| WO | WO-2014/016700 A2 | 1/2014 |
| WO | WO-2014/016700 A3 | 1/2014 |
| WO | WO-2014/016701 A2 | 1/2014 |
| WO | WO-2014/016701 A3 | 1/2014 |
| WO | WO-2014/047310 A1 | 3/2014 |
| WO | WO-2014/049448 A2 | 4/2014 |
| WO | WO-2014/049448 A3 | 4/2014 |
| WO | WO-2014/057361 A2 | 4/2014 |
| WO | WO-2014/057361 A3 | 4/2014 |
| WO | WO-2014/096969 A2 | 6/2014 |
| WO | WO-2014/096969 A3 | 6/2014 |
| WO | WO-2014/096971 A1 | 6/2014 |
| WO | WO-2014/096973 A2 | 6/2014 |
| WO | WO-2014/096973 A3 | 6/2014 |
| WO | WO-2014/207576 A2 | 12/2014 |
| WO | WO-2014/207576 A3 | 12/2014 |
| WO | WO-2015/004540 A2 | 1/2015 |
| WO | WO-2015/004540 A3 | 1/2015 |
| WO | 2015/139053 A1 | 9/2015 |

OTHER PUBLICATIONS

PCT International Search Report and Written Opinion for corresponding International Application Serial No. PCT/US2020/031266, dated Sep. 7, 2020, pp. 1-11.

Bailey (2011). "Activities of human genioglossus motor units," Respiratory Physiology & Neurobiology 179:14-22.

Cienfuegos et al., Mandible—Surgical approach—Intraocular—AO Surgery Reference, v1 .0 Dec. 1, 2008—(Accessed Apr. 18, 2016).

Cienfuegos et al., Mandible—Surgical approach—Submental—AO Surgery Reference, v1 .0 Dec. 1, 2008—(Accessed Apr. 18, 2016).

European Office Action corresponding to EP Application No. 14 809 219.0, dated May 2, 2017, 4 pages.

Final Office Action dated Jan. 10, 2011, for U.S. Appl. No. 14/547,400, filed Nov. 19, 2014, 14 pages.

Final Office Action dated Jun. 20, 2018, for U.S. Appl. No. 15/618,199, filed Jun. 9, 2017, 10 pages.

Final Office Action dated Apr. 23, 2019, for U.S. Appl. No. 15/618,199, filed Jun. 9, 2017, 9 pages.

Final Office Action dated Oct. 23, 2020, for U.S. Appl. No. 16/865,668, filed May 4, 2020, 14 pages.

Final Office Action dated Feb. 7, 2018, for U.S. Appl. No. 15/341,039, filed Nov. 2, 2016, 16 pages.

Final Office Action dated Aug. 17, 2021, for U.S. Appl. No. 16/865,668, filed May 4, 2020, 7 pages.

Final Office Action dated Jul. 27, 2021, for U.S. Appl. No. 16/507,390, filed Jul. 10, 2019, 13 pages.

International Search Report and Written Opinion dated Feb. 10, 2015, for PCT Application No. PCT/US2014/066311, filed on Nov. 19, 2014, 8 pages.

International Search Report and Written Opinion dated Oct. 9, 2020, for PCT Application No. PCT/US2020/031383, filed on May 4, 2020, 16 pages.

International Search Report and Written Opinion dated Sep. 8, 2020, for PCT Application No. PCT/US2020/031389, filed on May 4, 2020, 11 pages.

(56) References Cited

OTHER PUBLICATIONS

International Search Report and Written Opinion dated Aug. 14, 2020, for PCT Application No. PCT/US2020/031279, filed on May 4, 2020, 19 pages.
Non-Final Office Action dated Apr. 26, 2016, for U.S. Appl. No. 14/547,400, filed Nov. 19, 2014, 12 pages.
Non-Final Office Action dated Aug. 10, 2017, for U.S. Appl. No. 15/341,039, filed Nov. 2, 2016, 14 pages.
Non-Final Office Action dated Jan. 24, 2018, for U.S. Appl. No. 15/618,199, filed Jun. 9, 2017, 10 pages.
Non-Final Office Action dated Jan. 18, 2019, for U.S. Appl. No. 15/618,199, filed Jun. 9, 2017, 9 pages.
Non-Final Office Action dated Sep. 26, 2019, for U.S. Appl. No. 15/618,199, filed Jun. 9, 2017, 13 pages.
Non-Final Office Action dated Jan. 26, 2018, for U.S. Appl. No. 15/639,300, filed Jun. 30, 2017, 14 pages.
Non-Final Office Action dated Jan. 14, 2021, for U.S. Appl. No. 16/507,390, filed Jul. 10, 2019, 11 pages.
Non-Final Office Action dated Apr. 16, 2021, for U.S. Appl. No. 16/865,668, filed May 4, 2020, 8 pages.
Non-Final Office Action dated May 11, 2021, for U.S. Appl. No. 16/865,363, filed May 3, 2020, 10 pages.
Non-Final Office Action dated Jul. 15, 2021, for U.S. Appl. No. 16/870,292, filed May 8, 2020, 5 pages.
Notice of Allowance dated May 17, 2017, for U.S. Appl. No. 14/547,400, filed Nov. 19, 2014, 6 pages.
Notice of Allowance dated Apr. 5, 2018, for U.S. Appl. No. 15/341,039, filed Nov. 2, 2016, 9 pages.
Notice of Allowance dated Jan. 29, 2020, for U.S. Appl. No. 15/618,199, filed Jun. 9, 2017, 8 pages.
Notice of Allowance dated May 10, 2018, for U.S. Appl. No. 15/639,300, filed Jun. 30, 2017, 8 pages.
Schwartz, A.R. et al. (1996). "Electrical stimulation of the lingual musculature in obstructive sleep apnea," Journal of Applied Physiology 81:643-652.

\* cited by examiner

IMPLANTABLE STIMULATION POWER RECEIVER, SYSTEMS AND METHODS

CROSS-REFERENCE TO RELATED APPLICATIONS

This application claims the benefit of U.S. Provisional Application Ser. No. 62/841,978, filed May 2, 2019, the disclosure of which is hereby incorporated by reference in its entirety.

TECHNICAL FIELD

An implantable electrical stimulation device and system is provided herein. More specifically, the present disclosure relates to an implantable stimulator including an antenna for powering the stimulator via an inductive power coupling with an external controller. In one example, the stimulator can be implemented in, or as a portion of, a system, method, and apparatus for stimulating the hypoglossal nerve to treat obstructive sleep apnea.

BACKGROUND

Obstructive sleep apnea (OSA) is the most common type of sleep apnea and is characterized by repeated episodes of complete or partial obstructions of the upper airway during sleep, despite the effort to breathe, and is usually associated with a reduction in blood oxygen saturation. Individuals with OSA are rarely aware of difficulty breathing, even upon awakening. It is often recognized as a problem by others who observe the individual during episodes or is suspected because of its effects on the body. OSA is commonly accompanied with snoring. OSA can be associated with symptoms during the daytime (e.g. excessive daytime sleepiness, decreased cognitive functions). Symptoms may be present for years or even decades without identification, during which time the individual may become conditioned to the daytime sleepiness and fatigue associated with significant levels of sleep disturbance. Individuals who generally sleep alone are often unaware of the condition, without a regular bed-partner to notice and make them aware of the signs.

The most widely used current therapeutic intervention for treating OSA is positive airway pressure whereby a breathing machine pumps a controlled stream of air through a mask worn over the nose, mouth, or both. The additional pressure holds open the relaxed muscles. There are several mechanisms for treating OSA with positive airway pressure therapy. The most common treatment involves the use of continuous positive airway pressure (CPAP) machines. CPAP machines are worn by the OSA patient at nighttime during sleep, with the patient wearing a mask connected by hose to an air pump that maintains positive airway pressure.

Neurostimulation therapy can be an alternative for patients who cannot use a continuous positive airway pressure device. One neurostimulation system senses respiration and deliver mild electrical stimulation to the hypoglossal nerve (HGN) in order to increase muscle tone at the back of the tongue so it will not collapse over the airway. The HGN innervates the tongue musculature. It provides motor control for the muscles of the tongue and helps with important voluntary and involuntary functions like swallowing, speaking, and mastication. Stimulating the HGN can restore the tone to key tongue muscles that, when relaxed, can lead to obstructive sleep apnea.

Conventional HGN neurostimulation systems utilize stimulation leads implanted in the patient's neck/throat, with electrodes touching, e.g., a cuff electrode that surrounds the HGN or in close proximity to the HGN. The leads are connected via wire to a pulse generator implanted under the skin in the patient's chest. From time-to-time, the pulse generator is surgically accessed for battery changes. The system includes a handheld patient controller to allow it to be switched on before sleep.

While HGN neurostimulation therapy has proven to be an effective treatment for OSA, the bulk of the conventional systems and the degree of invasiveness in implanting, using, and maintaining the system is undesirable.

SUMMARY

In an aspect, a wireless implantable stimulator is provided. The stimulator can comprise an antenna for producing an induced current in response to being disposed in an electromagnetic field. The antenna can comprise a substrate having an upper surface and a lower surface, an upper coil comprising a plurality of coil turns disposed on the upper surface of the substrate, and a lower coil comprising a plurality of coil turns disposed on the lower surface of the substrate. The upper and lower coils can be electrically connected to each other in parallel.

DETAILED DESCRIPTION

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. As used herein, "stimulate" or "modulate" in the context of neuromodulation includes stimulating or inhibiting neural activity. A "patient" as described herein includes a mammal, such as a human being.

The present disclosure relates to an implantable electrical stimulation system 10, which can be used to provide a variety of electrical therapies, including neuromodulation therapies such as nerve and/or muscle stimulation. Stimulation can induce excitatory or inhibitory neural or muscular activity. Such therapies can be used at various suitable sites within a patient's anatomy. In one example implementation, the system 10 can be used to treat sleep disordered breathing (SDB) including obstructive sleep apnea (OSA) via neuromodulation of the hypoglossal nerve (HGN).

Electrical Stimulator System

Figure 1:
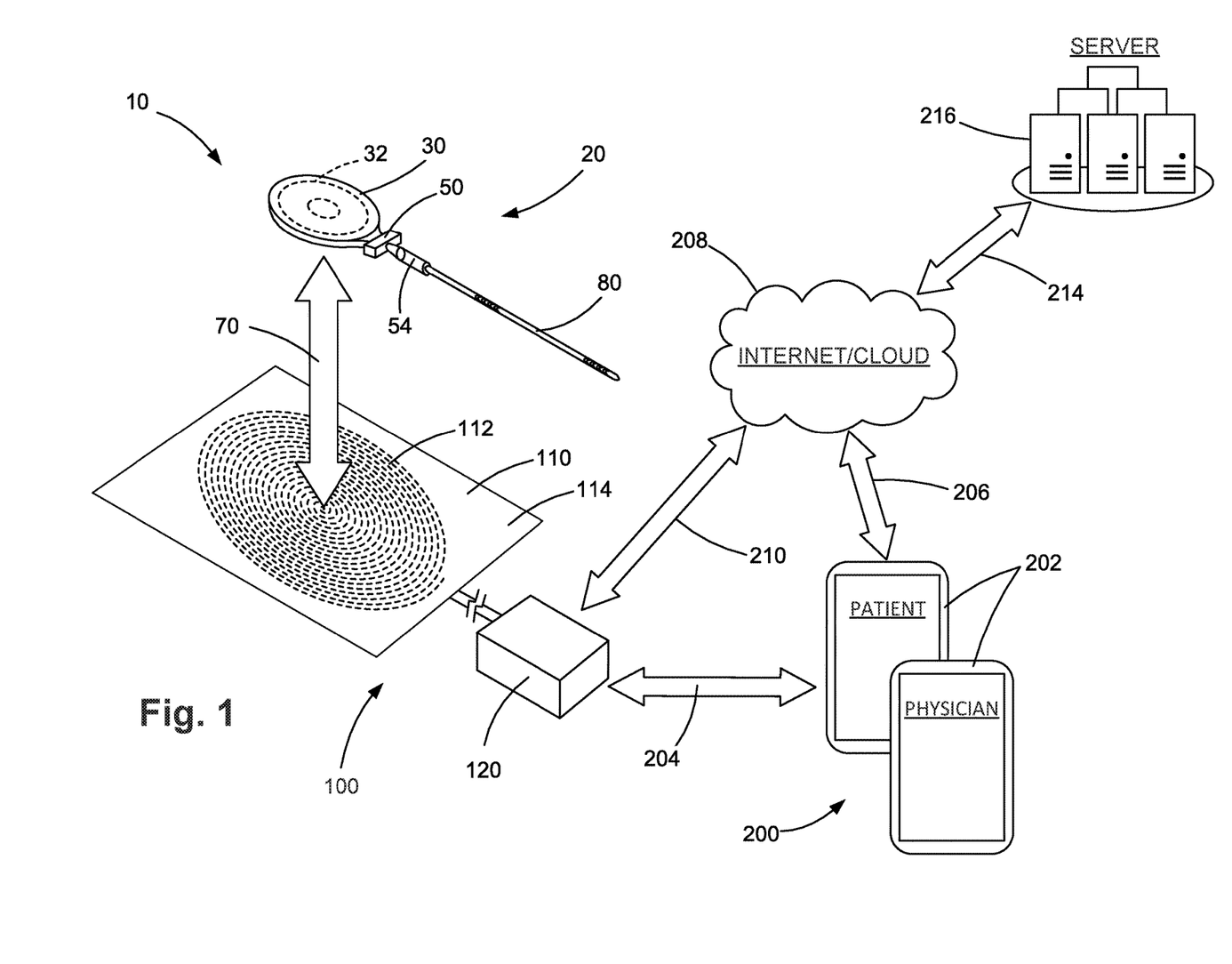
FIG. 1 is a diagram illustrating an example configuration of an implantable stimulation system according to an aspect of the present disclosure.

Referring to FIG. 1, the system 10 can include implantable stimulator 20 and external controller 100. Controller 100 can power stimulator 20 through electromagnetic induction. Stimulator 20 can include power receiver 30 with antenna 32. Electrical current can be induced in antenna 32 when it is positioned above power mat 112 of controller 100, in an electric field produced by power transmit antenna 112. Antennas 112 and 32 can also facilitate communication between controller 100 and stimulator 20, respectively. This power/communication link between stimulator 20 and controller 100 is shown generally by the arrow 70 in FIG. 1.

System 10 can also include a user interface 200 the form of a computer platform 202 running a custom application that enables communication with controller 100 wirelessly, as indicated generally by arrow 204. This can be done, for example, using Bluetooth or WiFi radio communication. In the example configuration of FIG. 1, computer platform 202 is a smartphone. The type of computer platform 202 could, however, vary. For example, the computer platform 202 can be a physician or patient platform. Each platform 202 can have an application or "app" installed thereon that is user specific, i.e., a patient app or a physician app. The physician platform would have the physician app installed, and the patient platform would have the patient app installed. The patient app can allow the patient to execute certain commands necessary for controlling operation of stimulator 20, such as, for example, start/stop therapy, increase/decrease stimulation power or intensity, and select a stimulation program. In addition to the controls afforded the patient, the physician app can also allow the physician to modify stimulation settings, such as pulse settings (patterns, duration, waveforms, etc.), stimulation frequency, amplitude settings, and electrode configurations, closed-loop and open loop control settings and tuning parameters for the embedded software that controls therapy delivery during use.

As indicated generally by arrow 206, computer platform 202 can be connected (e.g., WiFi and/or LTE) to internet/cloud 208, which facilitates communication 214 with remote or cloud-based server 216. This allows for the transfer of data between server 216 and computer platform 202 via internet 208. Additionally, controller 100 itself can also be internet connected (e.g., WiFi), as shown at 210. This can also allow for the transfer of data between controller 100 and server 216 via internet 208.

System Communication

As shown in FIG. 1 and described above, system 10 can be configured to provide various communication paths between the system components. For example, computer platform 202 being connected to controller 100 (see 204) and to internet 208 (see 206) can facilitate a communication path from remote server 216 (see 214) to stimulator 20 itself (see 70). A communication path between server 216 and stimulator 20 can also be established via WiFi link 210 of controller 100.

Additionally, recognizing that the physician may be remote from the patient, a physician communication path can be established via the internet connection 206 of the remotely located physician platform 202. Through this connection, remote physician platform 202 can communicate with server 216 through internet connection 206. Remote physician platform 202 can also communicate with controller 100, either via internet connection 210 (when enabled) or through patient controller 202.

In addition to facilitating local control of system 10, e.g., controller 100 and stimulator 20, the various communication paths described above can also enable:

Distributing from server 216 software/firmware updates for the computer platform 202, controller 100, and/or stimulator 20.

Downloading from server 216 therapy settings/parameters to be implemented by computer platform 202, controller 100, and/or stimulator 20.

Facilitating therapy setting/parameter adjustments/algorithm adjustments by a remotely located physician.

Uploading data recorded during therapy sessions.

Maintaining coherency in the settings/parameters by distributing changes and adjustments throughout the system components.

System Operation Overview

The therapeutic approach implemented with system 10 can involve implanting only stimulator 20, leaving controller 100 as an external component to be used only during the application of therapy. To facilitate this, stimulator 20 can be configured to be powered by controller 100 through electromagnetic induction. In operation, power mat 110, operated by control unit 120, can be positioned external to the patient in the vicinity of stimulator 20 to position transmitting antenna 112 of the controller, located in the mat, close to receiving antenna 32 of the stimulator. In the implementation where the system 10 is used to treat OSA, the power mat 110 can be positioned on or sufficiently near the sleeping surface while the patient sleeps to maintain the position of the receiving antenna 32 within the target volume of the electromagnetic field generated by the power antenna 112.

Through this approach, system 10 can deliver therapy to improve SDB such as OSA, for example, by stimulating the HGN, for example, through a shorter, less invasive procedure. The elimination of an on-board, implanted power source in favor of an inductive power scheme can eliminate the need for batteries and the associated battery changes over the patient's life.

Additionally, stimulator 20 can implement electromyography (EMG) electrodes for sensing neuromuscular responses to physiological needs of the patient during sleep. Such sensing electrodes can continuously monitor physiological intrinsic EMG signals from the anterior lingual musculature. For instance, EMG sensing electrodes can be configured to detect neuromuscular responses from the genioglossus muscle, which is innervated by the HGN.

Controller 100 can use transmitting antenna 112 for multiple purposes, for example: 1) to provide power to stimulator 20 during therapy sessions, and 2) to communicate with the stimulator. This communication can, for example, include programming, e.g., uploading software/firmware revisions to stimulator 20, changing/adjusting stimulation settings and/or parameters, and adjusting parameters of control algorithms. Controller 100 can receive the programming, software/firmware, and settings/parameters through any of the communication paths described above, e.g., from user interface 200 or through direct WiFi internet connection, when available. The communication paths can also be used to download data from stimulator 20, such as measured data regarding completed stimulation therapy sessions, to the controller 100. The controller 100 can transmit the downloaded data to the user interface 200, which can send/upload the data to server 216 via internet 208.

In operation, sensed EMG responses from the genioglossus muscle can allow closed-loop operation of the stimulator 20 while eliminating the need for a chest lead. Operating in closed-loop, the stimulator 20 can maintain stimulation synchronized with respiration, for example, while preserving the ability to detect and account for momentary obstruction. The stimulator 20 can also detect and respond to snoring, for example.

To facilitate real-time, closed-loop control, a control algorithm can be implemented locally on stimulator 20. This can be achieved, for example, by programming a control algorithm on an application-specific integrated circuit (ASIC) component of stimulator 20 (see below for the description of the stimulator electronics).

Operating in real-time, stimulator 20 can record data related to the stimulation session including, for example, stimulation settings, EMG responses, respiration, sleep state including different stages of REM and non-REM sleep, etc. For example, changes in phasic and tonic EMG activity of genioglossus muscle during inspiration can serve as a trigger for stimulation or changes in stimulation can be made based on changes in phasic and tonic EMG activity of the genioglossus muscle during inspiration or during different sleep stages. After the sleep session, this recorded data can be uploaded to user interface 200 and to server 216. Also, the patient can be queried to use the interface 200 to log data regarding their perceived quality of sleep, which can also be uploaded to the server 216. Offline, the server 216 can execute a software application to evaluate the recorded data to determine whether settings and control parameters can be adjusted to further optimize the stimulation therapy. The software application can, for example, include artificial intelligence (AI) models that, learn from recorded therapy sessions, how certain adjustments affect the therapeutic outcome for the patient. In this manner, through AI learning, the model can provide patient-specific optimized therapy.

Stimulator Configuration

Figure 2:
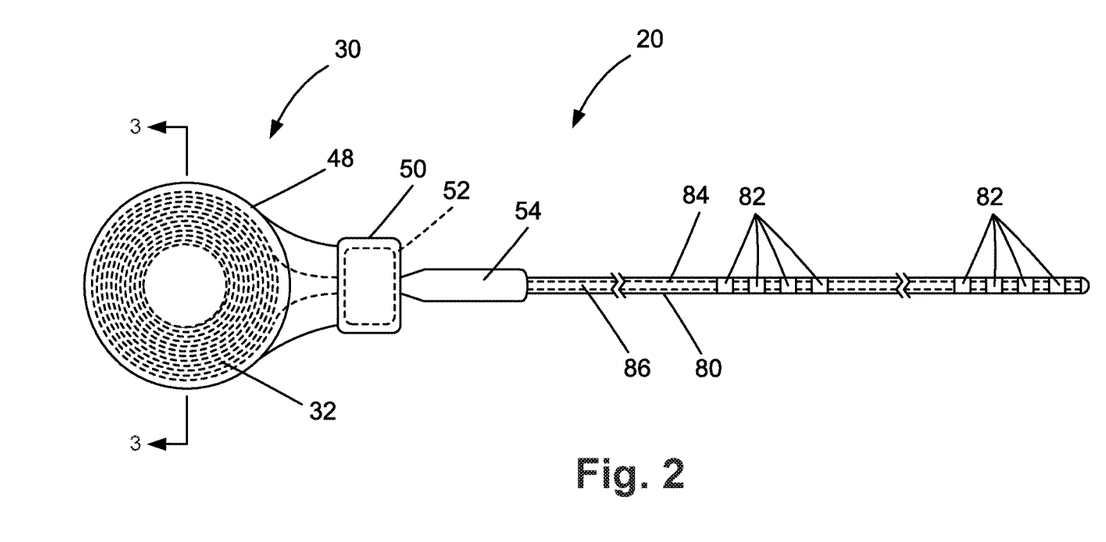
FIG. 2 is a schematic illustration of an implantable stimulator portion of an implantable stimulation system according to an aspect of the present disclosure.

The stimulator can have a variety of configurations, which can be tailored to the specific therapy being applied and/or to the anatomy at the site at which the stimulation therapy is applied. An example configuration of the stimulator 20 is illustrated in FIG. 2. Stimulator 20 can include power receiver 30, electronics package 50, and stimulator lead 80. Power receiver 30 can include a coiled receiver antenna 32 that is packaged in a protective biocompatible material and is operatively connected to the electronics package 50 and electronic components 52 mounted therein.

The stimulator lead 80 is also operatively connected to the electronics package 50, which controls the operation of the electrodes 82. In the example configuration of the present disclosure, stimulator 20 includes pigtail connector 54, which extends from electronics package 50 and can facilitate connecting stimulator lead 80 to the electronics package. Pigtail connector 54 can facilitate a detachable connection between electronics package 50 and stimulator lead 80 so that leads of different configurations can be connected to the electronics package. This can facilitate manufacturing of the stimulator lead 80. This can also allow a physician to select a lead having a desired size and/or configuration.

Additionally, the stimulator lead 80 being separate from, and connectable to, the remainder of the stimulator 20 via the pigtail connector 54, can facilitate implanting the lead separately. As a result, implanting the lead 80 can be much less invasive, allowing the lead to be placed via a small incision. An integrated design could necessitate a larger incision and also the need to handle and manipulate the entire stimulator 20 as a whole during the implantation process, which could complicate the lead placement, as the surgeon could have to work around the remainder of the stimulator 20, e.g., the electronics package 50 and the antenna 32.

Stimulator lead 80 can be generally elongated and includes a plurality of electrodes 82 spaced along its length. Electrodes 82 can be electrically connected to electronics package 50 by conductors, such as wires, that are illustrated schematically at 84 by dashed lines in FIG. 2. In the example configuration illustrated in FIG. 2, stimulator 20 has an eight-channel, eight electrode configuration, meaning that stimulator lead 80 includes eight electrodes 82, each having its own dedicated channel. Stimulator 20 can be configured to have a greater number of channels or fewer channels. Additionally or alternatively, stimulator 20 can include more than one lead, again depending on the specific therapy and/or the targeted anatomical structure. Regardless of the number of leads or channels, each electrode 82 can be configured and utilized independently of the other electrodes. Because of this, all or some of electrodes 82, whichever is determined to be most effective for a particular implementation, can be utilized during the application of stimulation therapy.

Electrodes 82 can be utilized as stimulating electrodes or sensing electrodes. Stimulating electrodes can used to apply stimulation to a target anatomical structure, such as, for example, a nerve or muscle. Sensing electrodes can be used to detect and measure an EMG response, for example, from a neuromuscular structure associated with the target nerve. For a SDB treatment implementation illustrated in this description, the target nerve can be the HGN and the associated muscle can be the genioglossus muscle. The stimulator can, however, be used to target other nerves and to measure physiological electrical signals from other anatomical structures, such as EMG responses, from other neuromuscular structures.

In the example configuration of FIG. 2, electrodes 82 are arranged in two groups of four electrodes spaced along the length of lead 80. One group of electrodes 82 can be positioned distally near an end of lead 80 and one group can be positioned proximally, between the distal group and electronics package 50. The configuration of electrodes 82 can, however, vary. The stimulator can include a different number of electrodes (two or more), and/or the electrodes can be grouped, spaced, or otherwise arranged in different configurations along the length of the lead. As mentioned previously, the stimulator can also include any suitable number of leads (one or more).

The identities of electrodes 82 as being stimulation electrodes or sensing electrodes can be determined by the manner in which they are controlled via electronics package 50. In certain implementations, the identities of electrodes 82 can be fixed. In a fixed implementation, certain ones of electrodes 82 can be assigned and used exclusively as stimulating electrodes and others can be assigned and used exclusively as sensing electrodes. In other implementations, the identities of electrodes 82 can be dynamic. In a dynamic implementation, electrodes 82 can be assigned and used as both stimulating and sensing electrodes. In further implementations, electrodes 82 can be implemented in combinations of fixed and variable identities.

How the electrodes are utilized depends at least in part on how the stimulator itself is implemented. In certain implementations of the stimulator, some or all of the electrodes can be positioned relative to structures, such as nerves and/or muscles for which both the application of stimulation energy and the sensing of an EMG response or other physiological electrical signal is desired. In these cases, some or all of the electrodes can be utilized as stimulating electrodes when stimulation at its location is desired, and as sensing electrodes when sensing at its location is desired. In other implementations of the stimulator, some electrodes can be positioned relative to structures for which only the application of stimulation energy is desired, and other electrodes might be positioned relative to structures for which only the sensing of EMG responses or other physiological signals is desired.

Advantageously, the identities of electrodes 82 is configured in software settings, and requires no hardware configurations. The selectable configurations of electrodes 82 can be facilitated by electronic components 52 enclosed in electronics package 50. Electronic components 52 are preferably implemented in an application-specific integrated circuit (ASIC). The electronic components 52 can, however, include one or more ASICs, discrete electronic components, and electrical connectors for connecting the electronic components to power receiver 30 and/or electrode lead 80. The electronic components, whether embodied in a single ASIC or one or more components, can, for example, include processing and memory components, e.g., microcomputers or computers-on-a-chip, charge storage devices (e.g., capacitors) for accumulating a charge and supplying stimulation power, and solid state switching devices for selecting the identities of the electrodes (e.g., anode, cathode, recording electrode) and modulating power supplied to the electrodes (e.g., pulse-width modulation (PWM) switches).

To provide comfort to the patient and ease of insertion for physicians, the stimulator 20 can have a generally soft/flexible construction. This soft/flexible construction can apply to lead 80, power receiver 30, or both the lead and the power receiver. In one example configuration, the stimulator components—power receiver 30, electronics package 50, and lead 80—can be coated or otherwise encased simultaneously in a single operation, such as an insert molding with a biocompatible material, such as silicone, epoxy, and various suitable polymers.

Figure 4:
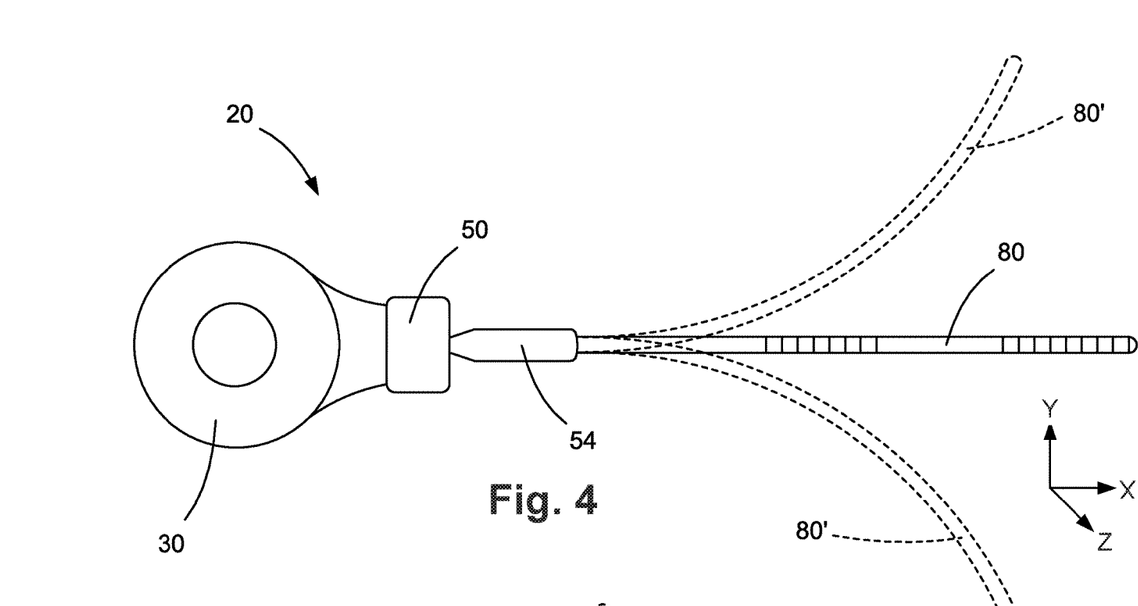
FIGS. 4-6 are schematic illustrations depicting flexible properties of an implantable stimulator according to an aspect of the present disclosure.
Figure 5:
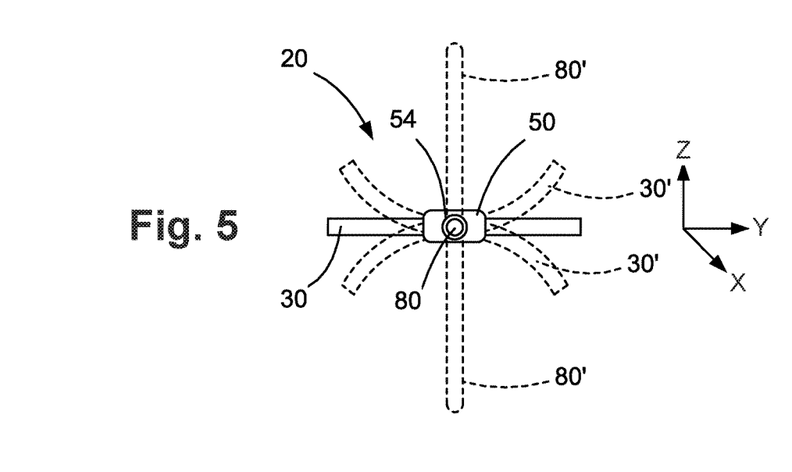
Figure 6:
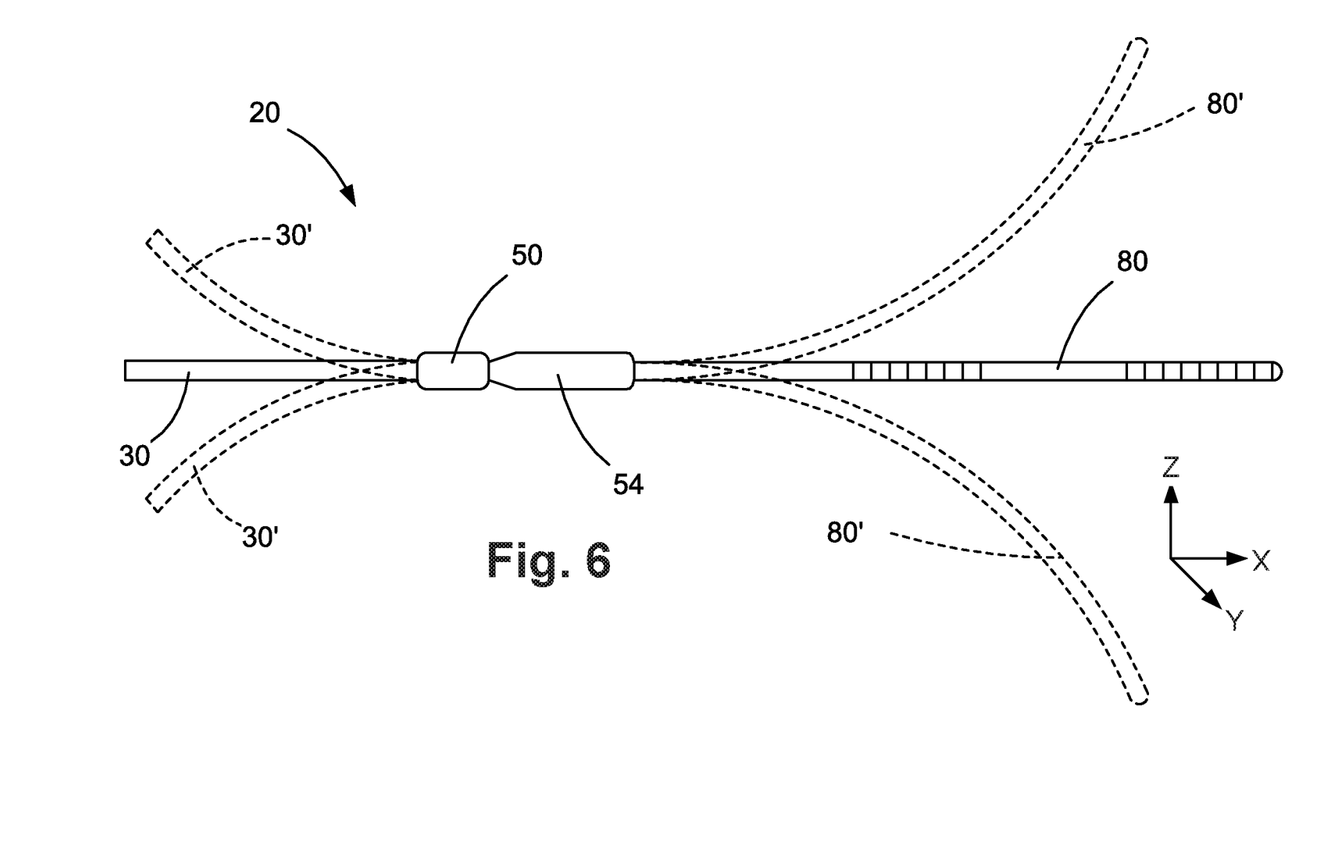

Referring to FIGS. 4-6, power receiver 30 and lead 80 can have a flexible configuration that allows either or both structures to bend or flex, which facilitates implantation compatibility with a variety of anatomical structures. Power receiver 30, can be generally flat and planar in configuration, and can bend in directions transverse to its plane which, as shown in FIGS. 4-6, is the X-Y plane. Power receiver 30 can thus bend in the Z-direction as shown in dashed lines at 30' in the Figures. Lead 80, can be generally elongated in configuration and can extend axially, along the X-axis as shown in FIGS. 4-6. Lead 80 can bend in multiple directions relative to that plane, i.e., in the direction of one or both of the Y-direction and Z-direction, as shown in dashed lines at 80' in the figures.

To facilitate the flexible configuration of lead 80, electrodes 82 and the conductors 84 (see FIG. 2) that connect the electrodes to the electronics package 50 can be encased and supported in a covering 86. Covering 86 can be formed of a biocompatible material, such as silicone and various suitable polymers, and can be configured to leave exposed electrodes 82 or portions thereof. Covering 86 can be formed, for example, in the aforementioned insert molded covering of the stimulator 20 structure.

To facilitate the flexible configuration of power receiver 30, antenna 32 can be formed on a soft substrate so as to be flexible and conform to the anatomy at the site of implantation. For example, power receiver 30 can have a flexible printed circuit board (PCB) construction in which antenna 32 is etched from a thin layer of conductive metal laminated on a substrate 38 (see FIG. 3) constructed of a flexible material, such as a polymer. In one particular flexible PCB construction, the substrate can be a polyimide material and the conductive metal can be copper. Other flexible PCB constructions can be implemented. Antenna 32 can be encased and supported in covering 48. Covering 48 can be formed of a biocompatible material, such as silicone, epoxy and various suitable polymers. Covering 48 can be formed, for example, in the aforementioned insert molded covering of the entire stimulator 20 structure.

The flexible PCB of power receiver 30 can extend into electronics package 50 and can be configured to mount the electronic components 52. The PCB can also be configured to interface conductors 84 of lead 80, and/or to form portions of the lead itself. In this instance, power receiver 30, electronics package 50, and lead 80 (or portions thereof) can be encased in the biocompatible material (e.g., silicone, epoxy and various suitable polymers) simultaneously.

While being flexible, the lead can also be configured to maintain a shape to which it is formed. This feature can, for example, be facilitated by conductors 84 that connect electrodes 82 to electronics package 50 or by an additional internal shape-maintaining (e.g., metal) support structure (not shown) that extends along its length. In either case, metal conductors 84 or the support structure can be selected or otherwise configured to possess physical properties, such as malleability/ductility, that allow the lead to be manipulated three dimensionally (3-D) into a desired shape or have a pre-determined bias and to maintain that shape or bias once formed. For example, the lead can be biased to have a certain shape that is created, for example, by heat shaping, material shaping or using other methods of manufacturing a biased lead.

Figure 7:
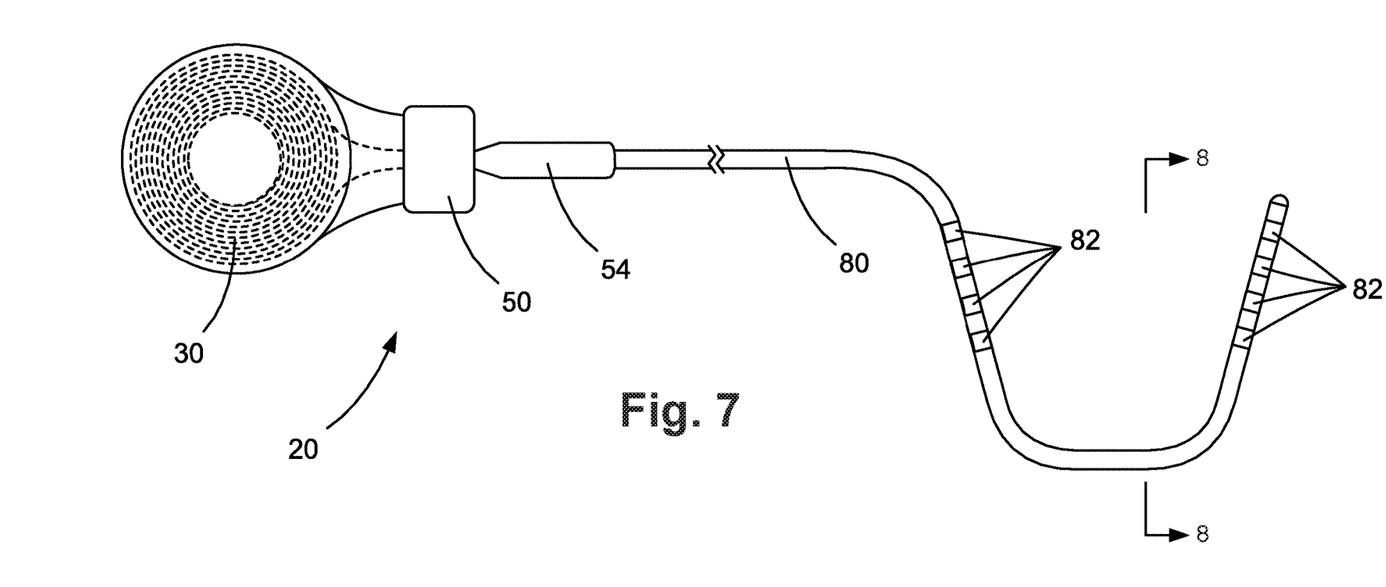
FIGS. 7-8 are schematic illustrations depicting an exemplary configuration of a lead portion of an implantable stimulator according to an aspect of the present disclosure.
Figure 8:
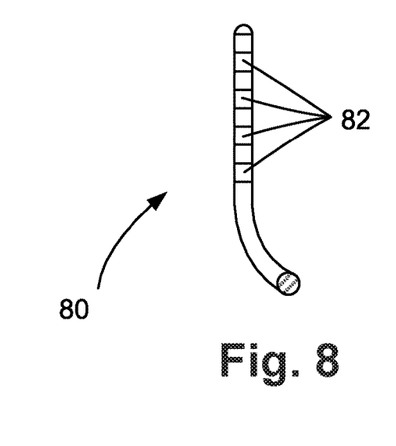

FIGS. 7-8 illustrate one such 3-D shape to which the lead 80 can be formed. The example configuration of FIGS. 7-8 shows the lead 80 formed three-dimensionally in a generally U-Shape or omega-shape, as shown in the plan view of FIG. 7, with an additional or alternative bend depth-wise as shown in FIG. 8. This particular 3-D configuration can be implemented to position the electrodes 82 at different positions along the HGN, where the stimulator is configured to treat SDB, such as OSA, for example. More specifically, the configuration of the lead 80 in FIGS. 7 and 8 can allow for the right and left electrodes 82 (as viewed in FIG. 7) to be placed in very close proximity to the HGN branches. The right and left electrodes 82 in an implanted configuration can extend along the posterior-anterior course of the HGN, placing the electrodes at or near the location of the branch points, such as distal branch points from the main trunk. This placement allows for direct electrical activation of a single branch or branches as needed for control of the posterior airway. In addition, with this implementation of lead 80, neurostimulation system 10 can be configured to stimulate bilaterally or unilaterally as needed without unnecessary or unwanted stimulation of surrounding structures. Because of the 3-D biased nature of the lead 80 and the synchronous manner in which the anterior lingual muscle move, additional anchoring structures may be unnecessary. For example, the inferior bend of the intermediate portion of the lead relative to the left and right electrode sets 82 when the stimulator is fully deployed can allow for force to be exerted against the genioglossus muscle by the lead, since the genioglossus muscle has a convex shape (when viewed inferiorly) to allow for better contact between the electrode sets and the genioglossus muscle The power receiver is designed with the goal of delivering maximum power to the stimulator from a given external magnetic field. With this goal in mind, for the HGN stimulation implementation of the example configuration disclosed herein, power receiver 30 and receiving antenna 32 have a unique configuration designed to adhere to several criteria for stimulator 20. The criteria depend, of course, on the intended therapeutic use of the system and the configuration resulting therefrom. The criteria set forth below are specific to an example configuration of system 10 for treating SDB including OSA via neuromodulation of the HGN:

- The stimulator 20 operates within the guidelines for maximum permissible magnetic field exposure as recommended in IEEE Standard C95.1-2005 (Reference 3).
- The receiving antenna 32 allows for near continuous power consumption (10-30 milliwatts (mW)) from the stimulator 20.
- The receiving antenna operates at a frequency ranging from 100 kHz to 2.4 GHz ISM (industrial, scientific, medical band of the radiofrequency spectrum). In one particular implementation, frequencies of 6.78 MHz or 13.56 MHz were used.
- The receiving antenna 32 has a diameter of 2-3 cm. and be as thin as possible to maintain flexibility.
- The stimulator 20 is small enough for minimally invasive subcutaneous implantation within the soft tissue of the sub-maxillary neck.
- The stimulator 20 maintains a soft, flexible design so that it can be manipulated to conform to the anatomy of the patient.

Other stimulation therapies or implementations of the implantable stimulation system 10 can cause some or all of these criteria to be changed or adjusted, and also for certain criteria to be added or removed.

Figure 3:
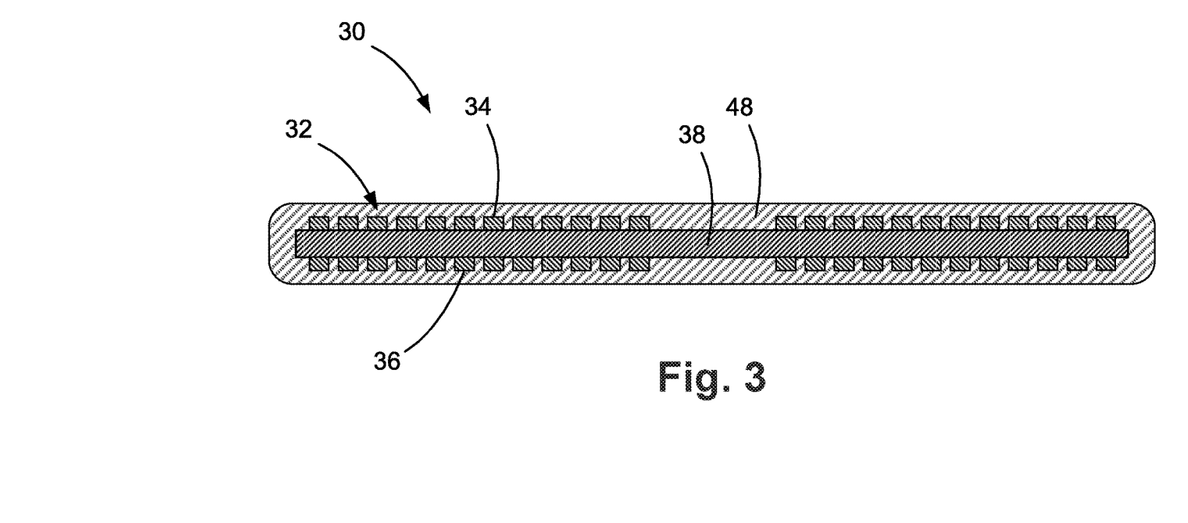
FIG. 3 is a section view taken generally along line 3-3 of FIG. 2, illustrating an antenna portion of the implantable stimulator.

To meet these criteria, receiving antenna 32 can have a double-layer, flat, "pancake" configuration. Referring to FIG. 3, antenna 32 can have a flexible PCB construction in which first or upper/top antenna coil 34 is formed on a first or upper/top side of substrate 38 and second or lower/bottom antenna coil 36 is formed on a second or lower/bottom side of the substrate. Substrate 38 can be a thin (e.g., 1 to 3 mil) polyimide layer and coils 34, 36 can be etched from thin layers of copper or gold (e.g., 1 oz./ft$^2$≈1.4 mil) laminated onto substrate 38.

PCB 38 can also support electronic components 52 in electronics package 50. Using guidelines for maximum permissible magnetic field exposure, IEEE Standard C95.1-2005 (which is incorporated herein by reference in its entirety), the maximum achievable delivered power is approximately 10-30 mW at 6.78 MHz frequency. These power requirements were chosen based on the estimated requirements for components 52 of electronics package 50, the estimated maximum stimulation parameters, and pre-clinical studies, while also including a safety factor to allow for capacitor charging and to provide transitional power. Transitional power can be provided via a variety of components, such as capacitors, supercapacitors, ultracapacitors, or even a rechargeable power source, such as a battery. Continuous power during patient movement, especially at the high end of power ratios and/or when coupling is not ideal. The transitional power source helps ensure complete, continuous operation of the stimulator 20, even during patient movement.

Those skilled in the art will appreciate that, in operation, an antenna can be susceptible to power losses due to substrate losses and parasitic capacitance between coils 34, 36 and between the individual coil turns. Substrate losses occur due to eddy currents in the substrate due to the non-zero resistance of the substrate material. Parasitic capacitance occurs when these adjacent components are at different voltages, creating an electric field that results in a stored charge. All circuit elements possess this internal capacitance, which can cause their behavior to depart from that of "ideal" circuit elements.

Advantageously, antenna 32 can implement a unique two-layer, pancake style coil configuration in which coils 34, 36 are configured in parallel. As a result, coils 34, 36 can generate an equal or substantially equal induced voltage potential when subjected to an electromagnetic field. This can help to equalize the voltage of coils 34, 36 during use, and has been shown to significantly reduce the parasitic capacitance of antenna 32. In this parallel coil configuration of antenna 32, top and bottom coils 34, 36 are shorted together within each turn. This design has been found to retain the benefit of lower series resistance in a two-layer design while, at the same time, greatly reducing the parasitic capacitance and producing a high maximum power output.

Figure 9A:
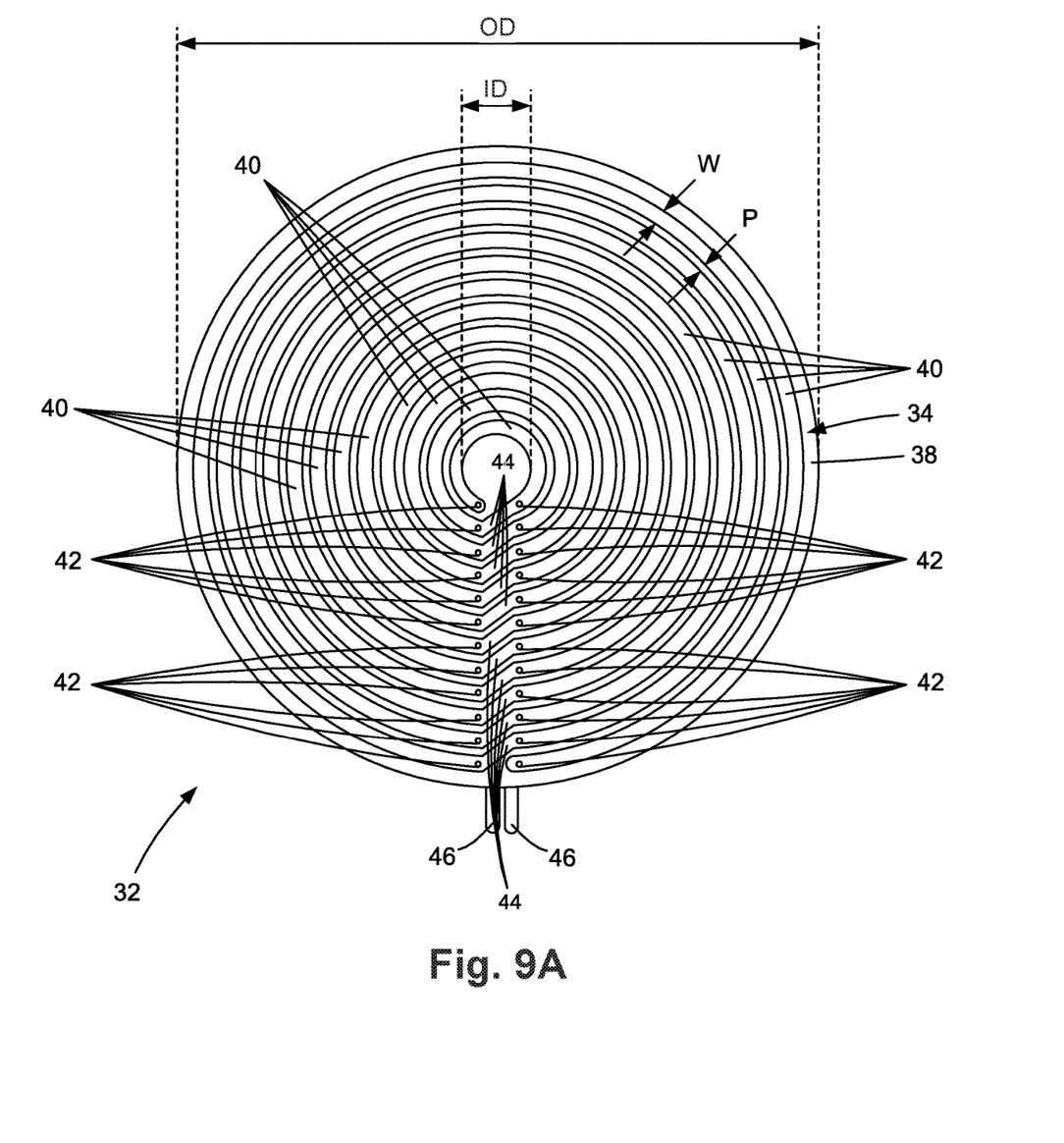
FIGS. 9A-9B are schematic illustrations depicting an exemplary configuration of an antenna portion of an implantable stimulator according to an aspect of the present disclosure.
Figure 9B:
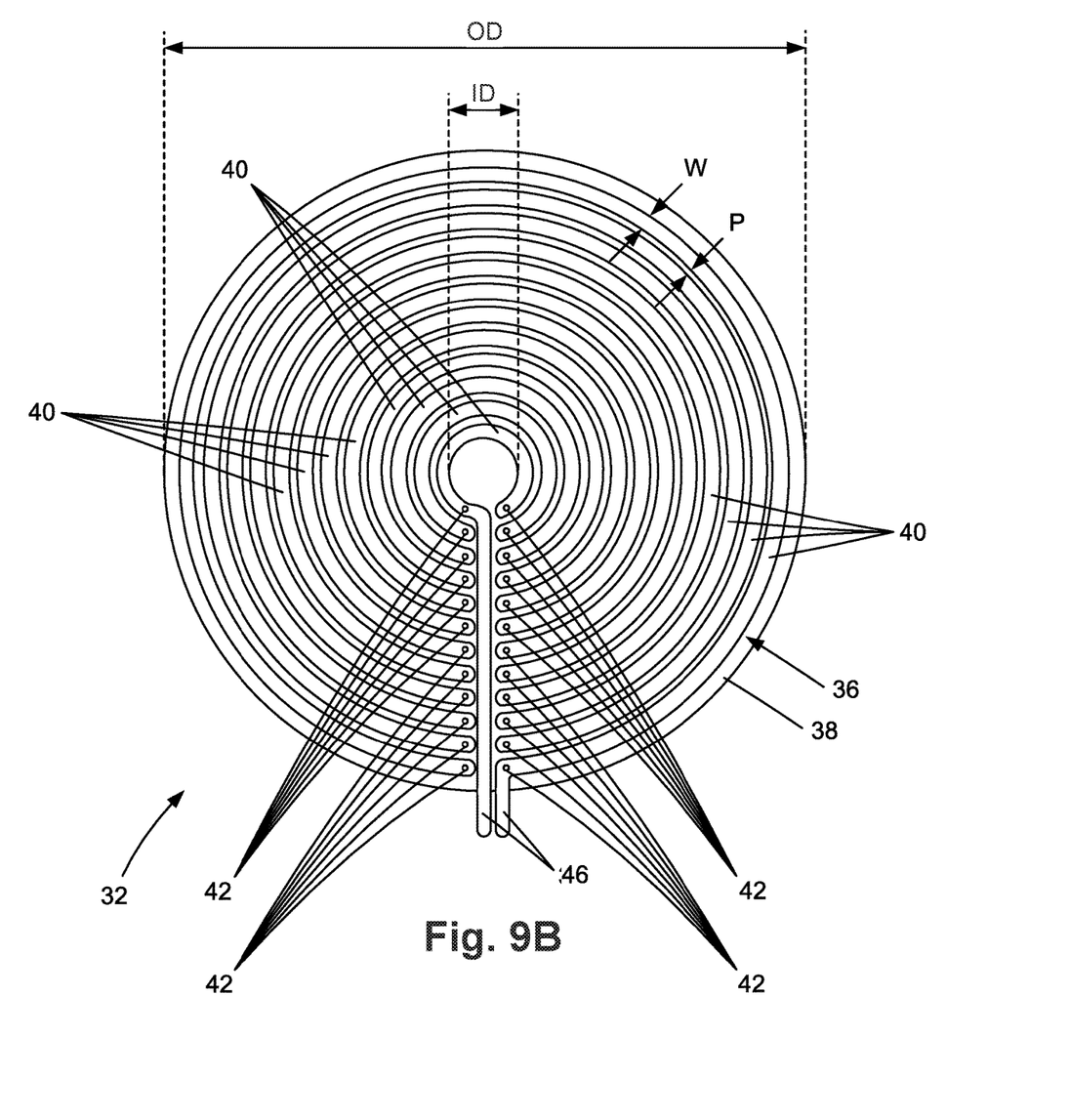

This improved, parallel configuration of antenna 32 is illustrated in FIGS. 9A and 9B, which illustrate the top and bottom coils 34 and 36, respectively, on PCB substrate 38. Each coil 34, 36 can include a plurality of coil windings or turns 40 and can be characterized by the following properties: number of turns (N), outside diameter (OD), coil pitch (P), trace width (W), trace thickness (T), and coil spacing (S). These properties are measured as follows:

- The OD is the diameter of coil 34, 36 measured across the coil between outer edges of outermost turn 40.
- The coil pitch P is the spacing between turns 40 measured between any two adjacent turns.
- The coil width W is the width of each coil turn 40.
- The trace thickness T is the thickness of turns 40, which is determined by the thickness of the conductive (Cu) layers laminated onto substrate 38 in the PCB construction.
- The coil spacing S is the distance between coils 34, 36, which is determined by the thickness of substrate 38 in the PCB construction.

In one particular configuration of antenna 32, PCB substrate 38 is a 2 mil polyimide layer and coils 34, 36 are etched from 1.4 mil copper laminated onto the substrate. The parallel coil configuration of the antenna 32 results from electrically connecting the turns 40 of the coils 34, 36 through substrate 38. These connections can be in the form of electrically conductive connectors illustrated at 42 in FIGS. 9A and 9B. Connectors 42 between the turns 40 can, for example, be formed by drilling or laser etching holes through the PCB structure, e.g., through substrate 38 and turns 40 of the upper and lower coils 34, 36, and plating or filling the holes with a metal, such as plated copper/gold or melted and/or flowed tin-lead, for example, to electrically connect the turns on the opposite surfaces of the substrate. The connectors could also be formed mechanically, e.g., pins or rivets.

Coils 34, 36 of antenna 32 have a unique configuration that allows for their parallel interconnection. On each side of antenna 32, turns 40 are circular, each having a fixed diameter with closely spaced ends. This is opposed to a traditional coil configuration in which the diameter of the turns varies continuously in a spiral that decreases progressively from outside to inside. To create the coiled configuration of the antenna 32, on one side of the antenna (upper coil 34 side in the example configuration of FIG. 9A), links 44 can extend diagonally between adjacent turns 40 of upper coil 34. Links 44 can be formed as portions of the copper layer, for example, laminated onto substrate 38, and therefore can be formed coextensively with turns 40 of upper coil 34 as one continuous conductive (Cu) strip. Upper coil 34 can therefore be configured as a continuous coil having decreasing diameter from outside to inside and can therefore function as a spirally configured coil.

On the lower coil 36 side of antenna 32, turns 40 can also be circular, each having a fixed diameter with closely spaced ends. There can be no links connecting adjacent turns 40 of lower coil 36. Instead, on the lower coil 36 side of antenna 32, terminals 46 can be formed—one connected to a terminal end of the innermost turn of the lower coil, and one connected to a terminal end of the outermost turn of the lower coil. Terminals 46 can be connected to innermost turn 40 and can extend in the space between the ends of the remaining turns.

Viewing FIGS. 9A and 9B, turns 40 of upper and lower coils 34, 36 can be interconnected at each of connectors 42. Through connectors 42, the links 44 interconnecting the adjacent turns 40 of the upper coil 34 can also interconnect the adjacent turns of lower coil 36. Thus, turns 40 of the lower coil 36 also can be arranged in a continuous coiled configuration through connectors 42 and links 44. Lower coil 36 therefore can be configured as a continuous coil having decreasing diameter from outside to inside and can therefore function as a spirally configured coil.

Terminals 46 can be electrically connected to both upper coil 34 and lower coil 36 through connectors 42. The terminal ends from which terminals 46 extend can be radially opposite ends of inner and outer turns 40. As shown, terminal 46 of innermost turn 40 is connected to a first end of the turn, on a first side of the space between the opposite ends of the turns; whereas the terminal of outermost turn 40 is connected to an opposite second end of the turn, on an opposite second side of the space between the opposite ends of the turns.

For the configuration illustrated in FIGS. 9A and 9B, the performance of the antenna can depend on the properties listed above. Example configurations of the antenna, for which some of these properties were adjusted, were tested. These example configurations are illustrated in the following table:

As shown in the above table, the maximum power delivered provided by each example coil configuration met or exceeded the 10-30 mW power requirement, even with the reduced coil outside diameter of Example 4.

The external controller 100 can have two components: power mat 110 and bedside control unit 120. Control unit 120 can be connected to power mat 110 by wire, for example, and is designed to be placed bedside, e.g., on a nightstand. The control unit can include a user interface, e.g., buttons, knobs, touchscreen, etc., to allow the user to control operation of the system when using the system in bed. Power mat 110 can be designed to be placed on the sleeping surface, such as a bed mattress, and therefore can be configured to have the form of a pad, e.g., a thin, flat, soft, flexible and non-slip configuration. Power mat 110 supports one or more wireless power transmit coils 112 in or on a flexible or semi-flexible surface 114. Power mat 110 can be positioned on the sleeping surface so that a lower edge 116 of the mat corresponds approximately to the position of the patient's shoulders while sleeping. The shape and size of the power mat 110 can correspond, for example, to that of a pillow, such as a queen size pillow.

Control unit 120 can excite power transmit coils 112 to generate an electromagnetic field. External controller 100 can utilize transmit coils 112 in power mat 110 to provide tethered wireless power transfer to stimulator 20 by way of receiving antenna 32 through electromagnetic induction. When the patient is in the sleeping position on the sleeping surface, antenna 32 of stimulator 20 can be positioned within the electromagnetic field produced by transmit coils 112 of power mat 110. The shape of the field can be tailored through the configuration of the coils 112 to provide a field that is optimized for powering the stimulator 20 through various sleeping positions. For example, the field can be configured extend horizontally (as viewed in FIGS. 10A-C) between the coils 112, so that the stimulator 20 can be powered any time it is positioned within the vertical bounds of the horizontally extending field.

Through induction, electric current can be induced in receiving antenna 32 and that current can be provided to stimulator electronics package 50. Components 52 in electronics package 50 control the operation of electrodes 82. Through this operation, electrodes 82 can be utilized as stimulating electrodes for applying electrical stimulation to nerves or muscles, for example; as EMG sensing electrodes, for example, for detecting a neuromuscular response, to the application of electrical stimulation; or as both stimulation and sensing electrodes at different times during the application of stimulation therapy.

In addition to providing power to stimulator 20, external controller 100 can also provide a data link for facilitating two-way communication between the controller and the stimulator. While powering the stimulator, controller 100 can simultaneously provide a wireless data signal that is used to program the stimulator with settings, such as electrode assignments and stimulation parameters, and also

| Property | Example 1 | Example 2 | Example 3 | Example 4 |
|---|---|---|---|---|
| Outer Diameter (OD) | 30 mm | 30 mm | 30 mm | 26 mm |
| # Turns (N) | 12 | 10 | 8 | 10 |
| Coil Pitch (P) | 1.0 mm | 1.0 mm | 1.0 mm | 1.0 mm |
| Trace Width (W) | 0.5 mm | 0.5 mm | 0.5 mm | 0.5 mm |
| Trace Thickness (T) | 1.4 mil | 1.4 mil | 1.4 mil | 1.4 mil |
| Coil Spacing (S) | 2 mil | 2 mil | 2 mil | 2 mil |
| Max. Power Delivery | 32.0 mW | 39.4 mW | 43.7 mW | 23.3 mW | retrieve stored data from the stimulator, such as triggered stimulation events, measured EMG responses or other electrical physiological signals, current values, electrode impedances, and data related to the wireless power transfer between controller 100 and stimulator 20.

Additionally, the stimulator 20 can monitor the impedance and/or voltage of the stimulator antenna 32 so that the power supplied to the stimulator can be calculated. This can be provided as feedback to the controller 100 that allows the controller to adjust the current supplied to the power transmit coils 112. The controller 100 can control the power delivered to the stimulator so as to remain within the standards/requirements set forth above. At the same time, the feedback can also facilitate increasing the current supplied to the power transmit coils 112 so that adequate power transfer to the stimulator 20 is maintained, again within the prescribed limits. In this manner, the controller 100 can implement closed-loop control to optimize the power supplied to the stimulator 20.

The operation of the controller 100 can be controlled through the user interface 200, which allows the user, e.g., the patient, physician or other caretaker, to control aspects of the operation of the implantable stimulation system 10. The control can be local, e.g., by the patient using a user interface of the control unit 120 or the patient user interface 200, or remote, e.g., by the physician through internet/cloud 208. The control unit 120 can have a small footprint and power mat 110 can be flexible in design so that external controller 100 is small, discreet, and portable for travel purposes.

Power Mat Configuration

To account for varying sleeping positions throughout the night, power mat 110 can have a large enough footprint to allow patient movement while still maintaining the ability to transmit power to stimulator 20. At the same time, external controller 100 does produce electromagnetic radiation at a level that falls outside the guidelines for maximum permissible magnetic field exposure as recommended in IEEE Standard C95.1-2005 (Reference 3).

Figure 10A:
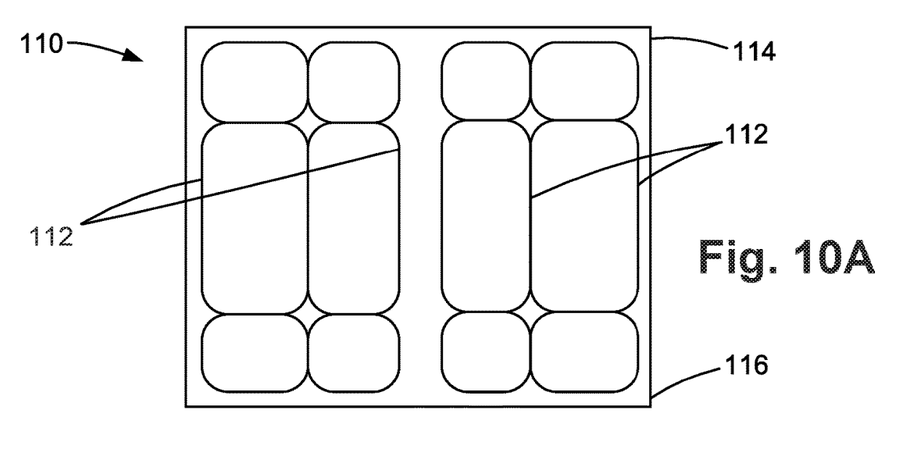
FIGS. 10A-10C are schematic illustrations depicting exemplary configurations of a power mat portion of an electrical stimulation system according to an aspect of the present invention
Figure 10B:
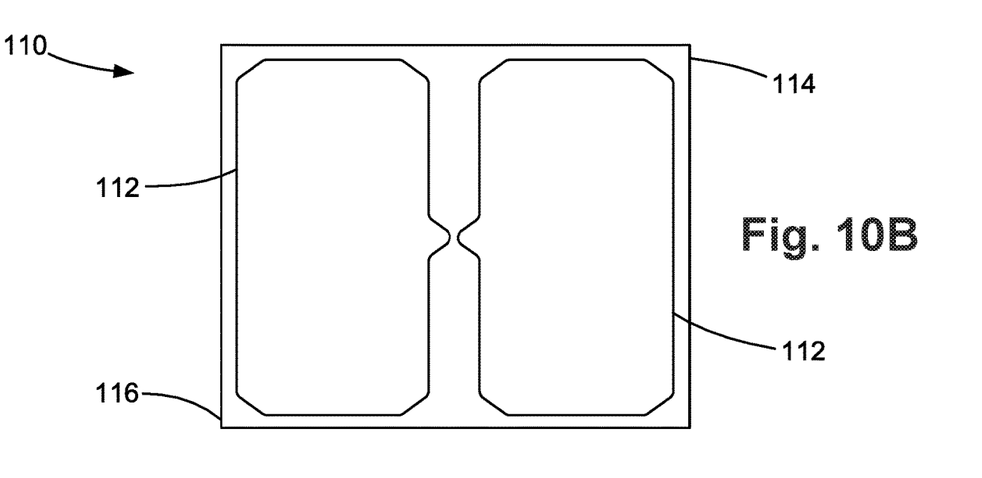
Figure 10C:
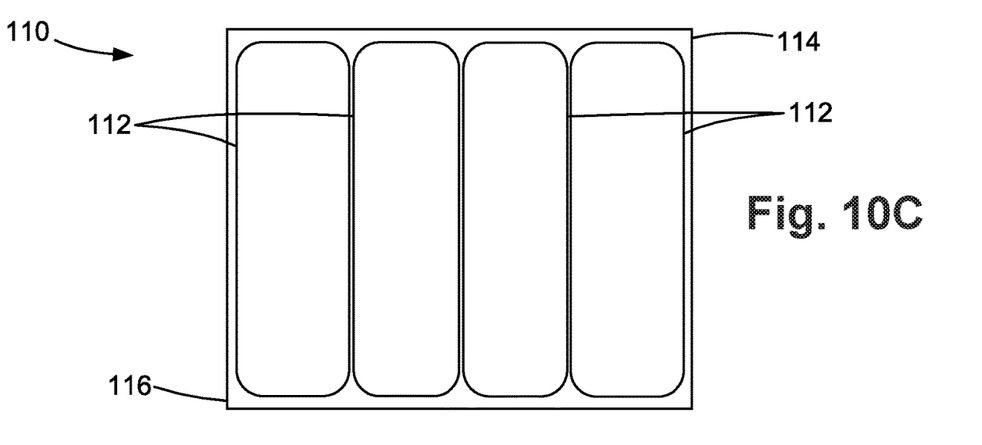

Example transmit coil configurations that can be implemented in power mat 110 are illustrated in FIGS. 10A-10C. These example transmit coil configurations can be implemented with a flex circuit design, i.e., the coils can be formed (e.g., etched) from a conductive metal (e.g., copper or gold) laminated on a flexible substrate (e.g., polyimide). The examples of FIGS. 10A-10C illustrate the overall shape of transmit coils 112 without showing the individual turns of the transmit coils. This is because the properties of the transmit coils 112, e.g., the number of turns, coil pitch/spacing, trace width, etc. is not limited, as can be the case with coils 34, 36 of antenna 32. Antenna coils 34, 36 can be tailored specifically for maximum induced power generation due to the small footprint limitations of antenna 32 of stimulator 20. Power mat 110 can be larger in comparison and transmit coils 112 can be free to be configured to produce a magnetic field that can be limited only by requiring a level that falls within the IEEE magnetic field exposure guidelines mentioned previously.

Accordingly, transmit coils 112 can be configured to maximize the space or volume that the magnetic field covers so as to allow for variations in the patient position during sleep. This can give the system the ability to continuously power the stimulator through a variety of sleeping positions throughout the night. FIG. 10A shows a twelve coil example configuration of transmit coils 112; FIG. 10B shows a two coil example configuration of transmit coils; and FIG. 10O shows a four coil example configuration of transmit coils. For all of these example configurations, experimental testing showed that transmit coils 112 are capable of meeting the system power requirements, within the IEEE exposure guidelines, while allowing for consistent power transfer to the antenna 32 over an effective volume of approximately 32×76×25 cm (L×W×H), which was found to be sufficient to cover the patient during a normal sleep cycle.

The twelve coil configuration of transmit coils 112 in FIG. 10A can allow for dynamic control of the magnetic field produced by the power mat 110. Through data coupling and communication between external controller 100 with stimulator 20, a determination can be made as to which coil(s) of the twelve coil configuration are effectuating the power coupling between the external controller and the stimulator. Through this determination, the external controller 100 can power only those coils necessary to power stimulator 20, given the current position of the patient relative to power mat 110. As the patient changes positions, the stimulator can detect any decrease in power transmission, which can trigger a reassessment and the selection of different coil(s). This configuration can thus be self-tuning, on-the-fly to maximize the electromagnetic field produced by the power mat 110 in the area of the antenna 32.

The two coil configuration of the transmit coils 112 in FIG. 10B can be static power coils that produce a continuous electromagnetic field around power mat 110. This configuration can be tuned to maximize the electromagnetic field strength in the largest possible volume so that power transmission is maximized throughout a wide variety of patient positions.

In the example configurations of both FIG. 10A and FIG. 10B, power mat 110 can have a flexible construction facilitated by a flexible circuit construction of transmit coils 112 housed within a flexible cover, such as, for example, soft plastic, rubber, fabric, etc. Transmit coils 112 can, for example, have a flexible PCB construction similar to antenna 32 of stimulator 20. For instance, transmit coils 112 can be constructed as a single layer flexible PCB, with conductive traces etched from copper, for example, laminated on a polyimide, for example, substrate.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Furthermore, all references cited herein are incorporated by reference in their entirety.

What is claimed is:

1. A wireless implantable stimulator comprising an antenna for producing an induced current in response to being disposed in an electromagnetic field, the antenna comprising a substrate, a first coil formed on a first surface of the substrate, and a second coil formed on a second surface of the substrate opposite the first surface, wherein the first coil comprises a plurality of first coil turns and the second coil comprises a plurality of second coil turns, wherein the first coil turns are aligned with corresponding second coil turns, and wherein first and second ends of each first coil turn are aligned with and electrically connected through the substrate to first and second ends, respectively, of a corresponding second coil turn such that the first coil turns are electrically connected in parallel to their corresponding second coil turns through the substrate.

2. The stimulator recited in claim 1, further comprising connectors that extend through the substrate and electrically connect the first coil turns formed on the first surface to their corresponding second coil turns formed on the second surface.

3. The stimulator recited in claim 2, wherein the connectors are configured to interconnect ends of the first coil turns to aligned ends of their corresponding second coil turns.

4. The stimulator recited in claim 2, wherein the first coil turns and the second coil turns are circular with opposite ends spaced apart from each other, and wherein the connectors interconnect ends of the first coil turns to aligned ends of their corresponding second coil turns.

5. The stimulator recited in claim 3, wherein the first coil further comprises electrically conductive links that interconnect first ends of the coil turns to opposite second ends of adjacent coil turns in the first coil.

6. The stimulator recited in claim 5, wherein the electrically conductive links span a gap between opposite ends of the adjacent coil turns.

7. The stimulator recited in claim 5, wherein the second coil does not comprise electrically conductive links that interconnect first ends of the coil turns to opposite second ends of adjacent coil turns in the second coil, and wherein the second coil comprises an electrically conductive lead electrically connected to an end of an innermost coil turn wherein the lead is configured to provide an electrical connection of the antenna with electronic components of the stimulator.

8. The stimulator recited in claim 1, wherein the antenna has a flexible printed circuit board construction, the substrate comprising a layer of polymer material, the first coil being etched from a layer of conductive metal material laminated onto a first surface of the polymer material, and the second coil being etched from a layer of conductive metal copper material laminated onto a second surface of the polymer material.

9. The stimulator recited in claim 8, wherein the polymer material is a polyimide material having a thickness of about 2 mils and the metal material of the first and second coils is copper having a thickness of about 1.4 mils.

10. The stimulator recited in claim 1, wherein the first and second coils each have 8-12 coil turns and a coil pitch of 1.0 mm.

11. The stimulator recited in claim 1, wherein the antenna has an outside diameter of 2-3 cm.

12. The stimulator recited in claim 1, wherein the antenna further comprises an outer coating constructed of a biocompatible material.

13. The stimulator recited in claim 1, wherein the antenna is flexible and is configured to conform to an anatomical structure at an implant site.

14. The stimulator recited in claim 1, further comprising an electronics package and a stimulation lead, wherein the antenna and the stimulation lead are electrically connected to the electronics package, the antenna being configured to supply electrical current to the electronics package to power the electronics package, the electronics package being configured to control the application of stimulation energy via the stimulation lead.

15. The stimulator recited in claim 14, wherein the stimulation lead comprises a plurality of electrodes, and the electronics package is configured to selectively control operation of the electrodes to apply electrical stimulation and to sense an EMG response.

16. The stimulator recited in claim 14, wherein the stimulation lead is configured to be bent to a desired shape and to maintain that shape in order to position electrodes relative to neurological and/or neuromuscular structures when implanted.

17. The stimulator recited in claim 1, wherein the first and second coils, by virtue of their being connected in parallel, are configured to produce a same induced voltage potential when subjected to an electromagnetic field.

18. The stimulator recited in claim 5, wherein the connectors and links are configured to electrically connect the first and second coil turns so that the first and second coils are spirally configured.

19. The stimulator recited in claim 18, wherein the connectors and links configure the first coil to extend spirally in a first direction, and wherein the connectors and links configure the second coil to extend spirally in a second direction, opposite the first direction.

20. The stimulator recited in claim 1, wherein the first coil turns and second coil turns are equal in number.

* * * * *